US007960604B2

(12) United States Patent
Tengberg et al.

(10) Patent No.: US 7,960,604 B2
(45) Date of Patent: Jun. 14, 2011

(54) PROCESS FOR PRODUCTION OF AN ABSORBING SANITARY ARTICLE COMPRISING LACTIC ACID PRODUCING BACTERIA

(75) Inventors: Hanna Tengberg, Göteborg (SE); Kristina Runeberg, Nällevikovögen (SE); Helene Jonsson, Helsingburg (SE); Endre Kvanta, Ängelholm (SE); Johan Burenius, Gothenburg (SE); Anna Weiner Jiffer, Danderyd (SE)

(73) Assignee: Ellen AB, Angelholm (SE)

( * ) Notice: Subject to any disclaimer, the term of this patent is extended or adjusted under 35 U.S.C. 154(b) by 670 days.

(21) Appl. No.: 10/398,249

(22) PCT Filed: Sep. 19, 2001

(86) PCT No.: PCT/SE01/01997

§ 371 (c)(1),
(2), (4) Date: Apr. 3, 2003

(87) PCT Pub. No.: WO02/28446

PCT Pub. Date: Apr. 11, 2002

(65) Prior Publication Data

US 2004/0172001 A1    Sep. 2, 2004

(30) Foreign Application Priority Data

Oct. 3, 2000  (SE) ....................... 0003544

(51) Int. Cl.
*A61F 13/15* (2006.01)
*A61F 13/20* (2006.01)

(52) U.S. Cl. ........ 604/360; 604/359; 604/367; 604/364; 604/368; 604/381; 604/385.01; 604/363; 424/93.45; 424/93.4; 602/48; 425/131.1; 264/13; 264/623; 264/638

(58) Field of Classification Search .......... 604/359, 604/360, 367, 364, 368, 381, 385.01, 363; 424/93.45, 93.4; 602/48; 425/131.1; 264/13, 264/623, 638
See application file for complete search history.

(56) References Cited

U.S. PATENT DOCUMENTS

| 3,691,271 | A | * | 9/1972 | Cherie et al. | 424/431 |
|---|---|---|---|---|---|
| 3,804,094 | A | * | 4/1974 | Manoussos et al. | 604/359 |
| 4,518,696 | A | * | 5/1985 | Gehrman et al. | 435/252.9 |
| 4,634,439 | A | * | 1/1987 | Sustmann et al. | 604/376 |
| 4,710,191 | A | * | 12/1987 | Kwiatek et al. | 424/449 |
| 4,883,478 | A | * | 11/1989 | Lerailler et al. | 604/360 |
| 5,211,971 | A | * | 5/1993 | Van Dijk et al. | 426/18 |
| 5,466,463 | A |   | 11/1995 | Ford |   |
| 5,681,646 | A | * | 10/1997 | Ofosu et al. | 428/198 |
| 5,685,872 | A | * | 11/1997 | Syverson | 604/360 |
| 5,883,199 | A | * | 3/1999 | McCarthy et al. | 525/437 |
| 6,020,453 | A | * | 2/2000 | Larsson et al. | 528/272 |
| 6,153,209 | A | * | 11/2000 | Vega et al. | 424/404 |
| 6,166,285 | A | * | 12/2000 | Schulte et al. | 604/364 |
| 6,187,990 | B1 | * | 2/2001 | Runeman et al. | 604/360 |
| 6,201,068 | B1 | * | 3/2001 | Tsai et al. | 525/178 |
| 6,359,191 | B1 | * | 3/2002 | Rusch et al. | 604/364 |
| 6,500,423 | B2 | * | 12/2002 | Olshenitsky et al. | 424/93.3 |
| 6,531,126 | B2 | * | 3/2003 | Farmer | 424/115 |
| 6,617,356 | B2 | * | 9/2003 | Goodman et al. | 514/565 |
| 6,854,600 | B1 | * | 2/2005 | Persson et al. | 206/494 |
| 7,048,950 | B2 | * | 5/2006 | Farmer | 424/522 |
| 2002/0094328 | A1 | * | 7/2002 | De Simone | 424/93.45 |
| 2003/0003138 | A1 | * | 1/2003 | Di Cintio et al. | 424/443 |
| 2003/0012810 | A1 | * | 1/2003 | Cintio et al. | 424/443 |
| 2004/0052759 | A1 | * | 3/2004 | Sawaki et al. | 424/74 |
| 2004/0191232 | A1 | * | 9/2004 | Farmer et al. | 424/93.45 |
| 2004/0243076 | A1 | * | 12/2004 | Husmark et al. | 604/358 |

FOREIGN PATENT DOCUMENTS

| CA | 2368509 A1 | 10/2000 |
|---|---|---|
| DE | 2 309 575 | 9/1974 |
| EP | 1212093 B3 | 7/2004 |
| EP | 1622652 A | 7/2007 |
| GB | 2 310 375 | 8/1997 |
| SE | 8505491-4 A | 11/1985 |
| WO | WO 84/04675 | * 12/1984 |
| WO | 92/13577 | 8/1992 |
| WO | WO-92/13577 A | 8/1992 |
| WO | WO 92/13577 A1 | 8/1992 |
| WO | WO 93/09793 A1 | 5/1993 |
| WO | 96/08261 A1 | 3/1996 |
| WO | WO 97/02846 A1 | 1/1997 |
| WO | 97/29762 | 8/1997 |
| WO | WO-97/29762 | 8/1997 |
| WO | 98/47374 | 10/1998 |

(Continued)

OTHER PUBLICATIONS

Notice of Opposition against EP1322346B1, Dec. 7, 2007.

(Continued)

*Primary Examiner* — Patricia M Bianco
*Assistant Examiner* — Ginger T Chapman
(74) *Attorney, Agent, or Firm* — Birch, Stewart, Kolasch & Birch, LLP

(57) ABSTRACT

The present invention relates to a process for the production of an absorbing sanitary article comprising lactic acid producing bacteria. The process comprises dispersion of lactic acid producing bacteria in a carrier, and application of the resulting dispersion of bacteria by continuous or discontinuous gentle feeding on and/or in at least one component that are to form part of the final article. Furthermore, the present invention relates to an absorbing sanitary article comprising lactic acid producing bacteria dispersed in an essentially hydrophobic carrier. The dispersion of bacteria forms at least one continuous or discontinuous string on and/or in the final sanitary article.

67 Claims, No Drawings

FOREIGN PATENT DOCUMENTS

| WO | WO 98/44884 | 10/1998 |
| WO | WO-98/47374 | 10/1998 |
| WO | WO 98/47374 A1 | 10/1998 |
| WO | 99/12504 | 3/1999 |
| WO | 99/12583 | 3/1999 |
| WO | WO-99/12504 | 3/1999 |
| WO | WO-99/12583 | 3/1999 |
| WO | WO 99/17813 | 4/1999 |
| WO | WO 99/45099 | 9/1999 |
| WO | WO-00/61201 A1 | 10/2000 |
| WO | 01/13956 | 3/2001 |
| WO | WO-01/13956 A2 | 3/2001 |

OTHER PUBLICATIONS

Declaration in the name of Dr. Husmark and Experimental Report "Storage stability of LB in wax", Nov. 28, 2007, as filed in Notice of Opposition.
Response to Notice of Opposition against EP1322346B1, May 9, 2008.
Weiner Jiffer, A. et al., "Stability Potential of Lactobacilli in Sanitary Tampons for Different Application Method—Evaluation Report," as filed with Response to Notice of Opposition dated May 9, 2008.
Annex to the Summons to Attend Oral Proceedings in European Patent No. 1322346-B1 dated Mar. 4, 2009.
Decision Revoking the European Patent No. 1322346-B1 dated Nov. 11, 2009.
Grounds for Appeal of the Decision to Revoke the European Patent No. 1322346-B1 dated Mar. 19, 2010.
Grounds for Decision in European Patent No. 1322346-B1 dated Nov. 11, 2009.
Information Result of Oral Proceeding in European Patent No. 1322346-B1.
Main Request in Oral Proceedings for European Patent No. 1322346-B1 dated Nov. 11, 2009.
Notice of Appeal in European Patent No. 1322346-B1 dated Jan. 11, 2010.
Notice of Opposition in European Patent No. 1322346-B1 dated Dec. 7, 2007.
Office Action 1 in Polish Application No. 360824 dated Sep. 19, 2001.
Office Action 2 in Polish Application No. 360824, filed on Sep. 19, 2001.
Proprietor's Response to the Letter to the Opponent dated May 4, 2009 and the Summons dated Mar. 4, 2009, to attend oral proceedings pursuant to Rule 115(1) EPC in European Patent No. 1322346-B1 dated Sep. 8, 2009.
Reply to the Summons dated Mar. 4, 2009 to attend oral proceedings pursuant to Rule 115(1) EPC in European Patent No. 1322346-B1 dated Apr. 23, 2009.
Request for Extension of Time in Opposition against European Patent No. 1322346-B1 dated Jul. 28, 2010.
Request for Oral Proceedings dated Oct. 5, 2009, before the Opposition Division on Oct. 8, 2009 in European Patent No. 1322346-B1.
Response and Auxiliary Request dated Sep. 8, 2009 to the Submission from the Proprietor dated May 9, 2008 in European Patent No. 1322346-B1.
Response to Notice of Opposition (Communication under Rule 79(1) EPC the proprietor of the Opposed Patent), received in European Patent No. 1322346-B1 dated May 9, 2008.
Submission from the Proprietor in preparation before the oral proceedings scheduled for Aug. 10, 2009 in European Patent No. 1322346-B1 dated Oct. 2, 2009.
Maness et al., "Bactericidal Activity of Photocatalytic TiO2 Reaction: toward an Understanding of Its Killing Mechanism", Applied and Environmental Microbiology, vol. 65, No. 9 (1999) pp. 4094-4098.
Exhibit D11 from Opposition in corresponding EP patent: Husmark U., Ph.D., "Storage stability of LB in wax," Apr. 16, 2009, pp. 1-3.
Exhibit D13 from Opposition in corresponding EP patent: Chung, C. et al., "An Antimicrobial TiO2 Coating for Reducing Hospital-Acquired Infection," Journal of Biomedical Materials Research Part B: Applied Biomaterials, 2007, pp. 220-224.
Exhibit D14 from Opposition in corresponding EP patent: Maness, P. et al., "Bacterial Activity of Photocatalytic TiO2 Reaction: toward an Understanding of Its Killing Mechanism," Applied and Environmental Microbiology, Sep. 1999, vol. 65, No. 9, pp. 4094-4098.
Exhibit D15 from Opposition in corresponding EP patent: Cheng, C., et al., "The effects of the bacterial interaction with visible-light responsive titania photocatalyst on the bacterial performance," Journal of Biomedical Science, 2009, vol. 16, No. 7, pp. 1-10.
Exhibit D8a from Opposition in corresponding EP patent: Figure 1: Wax 1 25 degrees C 65% r.h. (discussed, e.g., at p. 14 of Response and Auxilary Request dated Sep. 8, 2009 in EP Opposition 1322346-B1).
Opposition Papers filed in European Patent No. 1 322 346 B1, dated Oct. 18, 2010, pp. 1-17, including Exhibits D12, D16, D17, and D18.

* cited by examiner

PROCESS FOR PRODUCTION OF AN ABSORBING SANITARY ARTICLE COMPRISING LACTIC ACID PRODUCING BACTERIA

TECHNICAL FIELD

The present invention relates to a process for production of an absorbing sanitary article, preferably a tampon, comprising lactic acid producing bacteria.

Further, the present invention relates to an absorbing sanitary article comprising lactic acid producing bacteria.

TECHNICAL BACKGROUND

The skin of the urogenital tract and the urogenital mucus membranes of a healthy woman host a specific flora of beneficial and/or commensal microorganisms, such as various species of *Lactobacillus*. However, the urogenital tract can also be colonised by disease-causing microorganisms. The colonisation of unwanted microorgansims can be a result of sexual transmission, it can occur spontaneously or it can be the result of a disturbed normal microbial flora. The latter is, for instance, known to happen after certain antibiotic therapies.

Thus, the microbial flora of the female urogenital tract, such as in the vagina, may be disturbed and altered by a microbial infection, such as yeast (*Candida albinancs*), *Trichomonas vaginalis, Neisseria gonorrhoeae*, and *Chlamydia trachomatis*, and bacterial vaginosis (caracterized by increased prevalence of *Gardnerella vaginalis* and *Mobiluncus*), an antibiotic treatment or other often complex causes.

During menstruation and sexual intercourse, the pH in the vagina is increased by the addition of blood and sperm, respectively. These fluids contain a lot of proteins, which may be digested by bacteria (e g *Gardnerella vagnalis* and *Mobiluncus*), which might establish in the vagina under conditions of increased pH. Degradation products, such as amines (e g putrescine and cadacerine) are then produced. At increased pH, these amines become volatile and present a "fishy" odour. Additionally, these women often have complaints of increased vaginal discharge and irritation. This condition is called bacterial vaginosis (BV), and is the most common condition associated with irritation and increased amount of odorous vaginal discharge (see Morris, M; Nicoll, A; Simms, I; Wilson, J; Catchpole, M, Bacterial vaginosis: A public health review, British Journal of Obstetrics and Gynaecology, 108(5):439-450, May 2001).

Bacterial vaginosis is believed to be the result of displaced vaginal lactic acid producing bacteria which are replace by a range of unwanted species such as *Gardnerella vaginalis, Bacterioides, Mobiluncus, Prevotella bivia*, and *Mycoplasma hominis*.

It is known that lactic acid producing bacteria of the *Lactobacillus* strain dominate the flora of healthy women, and that most of these *Lactobacillus* bacteria have an ability to sustain the growth and reduce the pathogenicity of many uropathogens.

It is also known that the antagonistic properties of *Lactobacillus* and other lactic acid producing bacteria against pathogens are at least partially denoted by their ability of producing different so called antimetabolites, such as lactic acid, hydrogen peroxide, bacteriocins, etc.

Prior art describe formulations, such as suspensions, suppositories and gelatine capsules, comprising viable lactic acid producing bacteria. Such formulations are for instance disclosed in U.S. Pat. No. 5,466,463 and WO 9 309 793.

Furthermore, it is known to impregnate absorbent articles, such as tampons and sanitary napkins, with lactic acid producing bacteria for the purpose of preserving a normal flora of microorganisms in the urogenital tract of women, and thereby preventing urogenital infections, or regenerating a normal flora of microorganisms in the urogenital tract of women. Such a product is disclosed in EP 0 594 628.

An absorbing sanitary article comprising lactic acid producing bacteria is also disclosed in SE 8 505 491.

However, an applicable process for industrial production of such a product has not been described in prior art.

From WO 9 917 813 it is known, in a laboratory scale, to spray an aqueous bacteria suspension onto a sanitary napkin with a subsequent drying step.

EP 0 594 628 describes application of bacteria to a sanitary article by coating the sanitary article with a bacteria suspension or by dipping the article in such a suspension. The suspension consists of bacteria suspended in a carrier. The only mentioned purpose of this carrier is that it acts as an adhesive between the bacteria and the sanitary article.

Nevertheless, during an industrial manufacturing process, the bacteria are exposed to very extreme conditions, which are generally not comparable to laboratory conditions. To obtain an operating product, it is of crucial importance that a major part of the bacteria survive these manufacturing conditions, and that the absorbing sanitary article may be stored for a long time, i.e. a long shelf life for the bacteria in the sanitary article is achieved. Since bacteria are sensitive to, for instance, moisture, temperature, oxidation, and mechanical influence, these above-mentioned objects are not easy assignments to solve.

SUMMARY OF THE INVENTION

The object of the present invention is to present a well-functional process for the production of an absorbing sanitary article, e.g. a tampon, a sanitary napkin or a panty liner, comprising lactic acid producing bacteria in the viable state. It is crucial that a major part of bacteria survive the process. The bacteria in and/or on the sanitary article will propagate in contact with body fluids of the urogenital tract of the individual using the sanitary article.

The absorbing sanitary article is to be used as a probiotic for preserving and/or regenerating a normal flora of microorganisms in the urogenital tract, particularly in the vagina, of women.

The above object is achieved by dispersing the bacteria in a carrier, which results in a dispersion of bacteria. This dispersion is applied by gently feeding it on and/or in at least one component that is to form part of the final absorbent article. The gentle feeding is preferably performed by extrusion.

Application by gentle feeding, preferably extrusion, is a gentle application method. The mechanical stress on the bacteria is minimal using gentle feeding compared to, for instance, spraying.

Furthermore, the dispersion of bacteria is preferably applied before the final absorbent article is formed, that is, in a step during the manufacturing of the article. The application may be performed on and/or in at least one component that are to form part of the final product. Such a component may be cellulose and/or viscose fibres, super-absorbents, a web, a sliver, or a fabric. (A sliver might also be referred to as card ribbon or card tape.) This component may be in the form of an internal and/or an external layer in the final absorbing article.

It is preferred to apply the dispersion of bacteria in such a way that a major part of the bacteria is kept inside the final absorbent article. The bacteria are thereby better protected against the environment, for instance, against moisture and air than if applied onto the surface of the article. The dispersion of bacteria may e.g. be applied onto fibres that later on in the manufacturing process form a web.

The dispersion is preferably applied by extrusion onto a web or a sliver, most preferably a web.

The carrier reduces the mechanical stress on the bacteria, and protects the bacteria from air. The risk of bacteria protein oxidation is thereby reduced.

Preferably, the carrier is essentially hydrophobic, since the carrier then acts as a moisture and water repellent. Thus, the carrier also protects the bacteria against moisture and water.

Furthermore, a carrier is used since it is easier to apply a dispersion than, for example, freeze-dried bacteria alone onto a component.

The carrier also keeps the bacteria in or on the absorbent article, and reduces bacteria loss due to poor adhesion between the bacteria and the material of the absorbent article.

It is of great importance that the dispersion is easy to handle, e.g. to pump, and that the bacteria do not sediment in the dispersion. If the bacteria sediment before application to the absorbent article, there is a risk that the products will not be uniform. This means that the amount of bacteria in and/or on the sanitary articles may vary, which, for instance, may result in that an article even could be without bacteria. The viscosity is therefore an important property of the carrier. The viscosity is preferably 200-20 000 mPas, more preferably 1 000-3 000 mPas, measured at 30° C. with a shear rate of 100 1/s with a cone (diameter 50 mm, 2°).

Thus, it is an object to obtain a stable dispersion. This may be facilitated by the addition of a dispersing agent, such as a polysorbate.

Most preferably the carrier comprises fatty acids, i.e. the carrier may be a fat, an oil, a wax, etc.

First of all, a carrier comprising fatty acids is hydrophobic.

Secondly, a carrier comprising fatty acids may exist both in molten, semi-solid or solid form. It is preferred that the carrier is a fat in semi-solid/solid form at normal conditions, i.e. ambient temperature, since the absorbent article then is easier to handle for e.g. the user. Further, to obtain a homogeneous dispersion the bacteria are preferably added to a carrier that is either in the molten state or semi-solid.

To allow the release of bacteria from the carrier during use of the absorbent article, the fat should be in melted form in contact with the body of the user. Thus, the fat should preferably have a melting temperature between approximately 25° C. and 45° C., more preferably 30-37° C.

Furthermore, the fat is preferably at least partially saturated. This is to minimise the risk of fat degradation due to oxidation.

When using an essentially hydrophobic carrier, only a part of the article should comprise dispersion of bacteria. In aspect of absorption of body fluids, such as hydrophilic blood, the hydrophobic area of the article should be minimised.

The dispersion may be applied in at least one dot, spot, and/or string. However, the dispersion is preferably applied in at least one continuous or discontinuous string.

A string is also preferred since surrounding bacteria and carrier material will protect every single bacterium. If the dispersion is spread over a larger area, e.g. by spraying, the distance between one bacterium and another is increased, and there is less carrier material surrounding each bacterium. Thus, the bacteria are better protected against the environment if the dispersion is applied in a string.

Additives, such as a colouring agent or pigment, may be comprised in the dispersion. Metal oxides, e.g. zinc oxide, titanium oxide or a mixture of these, may for instance be added to mask the appearance of the dispersion of bacteria in the absorbing article. These substances mask the generally yellowish colour of the bacteria.

To increase the survival and reproduction of the bacteria and its production of lactic acid and other metabolites, nutrients may be added to the dispersion. For instance carbohydrates, such as maltodextrin, glucose, fructose, maltose, lactulose, dextrose, arabinose, mannose, galactose, salicin, etc, and vitamins, such as vitamin B and/or E and/or complexes thereof, may be added.

The lactic acid producing bacteria used are preferably isolated from the urogenital tract of a healthy woman with a normal bacterial flora.

The most preferred bacteria are chosen from the group consisting of the following bacteria strains: *Pediococcus*, *Lactobacillus* and *Lecuconostoc*.

The bacteria are preferably freeze-dried before they are dispersed in the carrier. Freeze-drying is a very gentle drying process compared to, for instance, spray drying.

The present invention also relates to a process for the production of an absorbing sanitary article, e.g. a tampon, a sanitary napkin or a panty liner, comprising viable lactic acid producing bacteria, wherein the bacteria are dispersed in an essentially hydrophobic carrier and applied by any application method on and/or in at least one component that are to form part of the final article, and where the mentioned component(s) is/are fibres, super-absorbents, a web, a sliver and/or a fabric. The application may, e.g., be spraying or gentle feeding (e.g. discontinuous or continuous extrusion).

Furthermore, the present invention relates to an absorbing sanitary article produced according to any of the processes described above.

An absorbing sanitary article comprising at least one continuous or discontinuous string of bacteria dispersed in an essentially hydrophobic carrier is also comprised within the scope of the present invention.

Other features and advantages of the present invention will become apparent from the following description of the invention.

DETAILED DESCRIPTION OF THE INVENTION

As used herein the term "absorbing sanitary article" means tampons (both digital tampons and tampons with an applicator), sanitary napkins, panty liners, diapers, incontinence guards and the like.

As used herein the term "lactic acid producing bacteria" means bacteria that by fermentation produce lactic acid.

As used herein the term "carrier" means a substance in which the bacteria may be dispersed., Such a substance is preferably semi-solid/solid at ambient conditions. However, it might also be an aqueous or non-aqueous liquid or solution.

The carrier is preferably essentially hydrophobic. As used herein the term "essentially hydrophobic" means essentially water-repellent.

As used herein the term "dispersion" means a mixture that comprises at least two phases. One phase constitutes of essentially solid particles (the dispersion is a suspension) or liquid (the dispersion is an emulsion), and this phase is dispersed in the other phase (the continuous phase).

As used herein the term "gentle feeding" means that a material is feed by the use of e.g. a screw feeder and/or a pump. It is preferred, but not necessary, that the feed is applied through a nozzle.

As used herein the term "component" means that it is to form part of the final product, i.e., for instance, a starting material or an intermediate product. At the manufacturing of, for example, a tampon, the starting material is cellulose fibres or viscose fibres. From these fibres a web is made. Thus, the web is an intermediate product. Another intermediate product is a sliver, which may be formed from a web.

At the manufacturing of, for example, a sanitary napkin, the starting material may be, e.g., a super-absorbent or a fabric.

Furthermore, the component may, for instance, be an internal or external layer in the final absorbing article.

As used herein the term "continuous or discontinuous string" means a continuous line or a discontinuous line of dots, spots, shorter lines, etc. A broad continuous string may be called a layer or a film.

As used herein the term "part of the final sanitary article" means not the entire sanitary article.

As used herein the term "normal flora" means the urogenital flora of a healthy woman.

As mentioned earlier it is of crucial importance that a major part of the bacteria survive the manufacturing process, and that the absorbing sanitary article may be stored for a long period of time.

The present invention provides a process for manufacturing of a sanitary article, e.g. a tampon, a sanitary article or a panty liner, comprising lactic acid producing bacteria that are viable under a surprisingly long period of time.

A long shelf life is provided by means of one, preferably more than one, and most preferably all, of the following factors:
a) application of bacteria by gentle feeding, preferably extrusion,
b) dispersion of the bacteria in a carrier, preferably an essentially hydrophobic carrier, before application,
c) application on and/or in a component, such as fibres, super-absorbents, a web, a sliver, and/or a fabric, and/or
d) a string of dispersion of bacteria in and/or on the final sanitary article.

Gentle feeding, by for instance extrusion, is a very gentle application method as compared to, for example, application by spraying. The mechanical stress on the dispersion, hence the bacteria, is minimised using extrusion.

It was, however, found that spraying has a negative impact on the bacteria viability, most likely due to the high mechanical stress on the bacteria during spraying.

Other negative aspects of spraying was revealed by some initial experiments performed by the inventors. These drawbacks are illustrated in the following description of these exepriments.

One of the initial experiments was to spray coconut butter on a sliver during the manufacturing process of a tampon. Fat was applied over the entire sliver. However, it was very difficult to control the amount of fat applied on the sliver. Moreover, the spray nozzle distributed the fat unevenly, i e more fat in the centre of the spray and less in the periphery, which resulted in an uneven distribution of fat on the sliver. Furthermore, the fat had to be heated to about 40° C. to allow spraying (the viscosity had to be decreased). Another problem was clogging of the spray nozzle. During manufacturing, the machine parts were covered with hot fat and thus slippery, and as a consequence the tampon machine was unable to fold the sliver into tampons.

Another experiment was to spray the fat on a conventional surface layer of non-woven, which after application was applied on a tampon (without surface layer). However, besides those above-disclosed problems with spraying, the roller of the tampon machine slipped due to the applied fat during application of the surface layer on the tampon.

Yet another experiment was to apply a dispersion of bacteria in Acosoup (from Karlshamns AB) in tampons, which had not yet been compressed. The dispersion was manually applied inside the tampons with a syringe. However, during the compression step the dispersion was squeezed out from the tampon since the fat was to hard at room temperature. Thus, a similar experiment was performed with coconut butter, which is much softer at room temperature than Acosoup. Since this fat spread out more inside the tampon, it remained in the tampon during the compression. However, due to the spreading of the fat, the liquid absorption of the fibres of the tampon was impaired.

From these experiments it was concluded that spraying was not a desirable application process.

Furthermore, it was concluded that the characteristics of the carrier is important for obtaining the desired product.

The carrier facilitates the application and protects the bacteria in several aspects.

First of all, the carrier reduces the mechanical stress on the bacteria.

Secondly, it is easier to apply a dispersion than for instance freeze-dried bacteria alone. In addition, the carrier acts as an adhesive between the bacteria and the component that the bacteria are applied to.

Thirdly, the carrier protects the bacteria from, or reduces, contact between bacteria and air and humidity. Hence, the risk of protein oxidation of the bacteria is decreased. An essentially hydrophobic carrier also protects the bacteria from contact with moisture and water, and a better stability of bacteria is thereby achieved.

Most preferably the carrier comprises fatty acids, i.e. the carrier may be a fat, an oil, a wax, etc.

First of all, a carrier comprising fatty acids is hydrophobic.

Secondly, a carrier comprising fatty acids may exist both in molten, semi-solid or solid form. It is preferred that the carrier is a fat in semi solid/solid form at normal conditions, i.e. at ambient temperature, since the absorbent article then is easier to handle for e.g. the user. Further, to obtain a homogeneous dispersion the bacteria are preferably added to a carrier that is either in the molten state or semi-solid. A semi-solid substance is also easier to handle, e.g. to pump, during the manufacturing of the aforementioned absorbing sanitary article.

To allow release of bacteria from the carrier during use of the absorbent article, the fat should be in melted form at use of the sanitary article. Thus, the fat should preferably have a melting temperature between approximately 25° C. and 45° C., more preferably 30-37° C. This melting temperature range is also preferred with consideration to preparation and application of the dispersion. As known to a skilled person in the art, the bacteria do not survive high temperature.

When the lactic acid producing bacteria are released in the urogenital tract they propagate, and the advantages of lactic acid producing bacteria according to the introduction and EP 0 594 628 are thus obtained.

In a preferred embodiment the carrier is at least partially saturated fat, with a viscosity of 200-20 000 mPas, more preferably 1 000-3 000 mPas, measured at 30° C. with a shear rate of 100 1/s with a cone (diameter 50 mm, 20), and a melting temperature between approximately 25° C. and 45° C., more preferably 30-37° C.

Fat is, advantageously used, and is preferably at least partially saturated to minimise the risk of fat oxidation.

The dispersion should preferably be at least semisolid at operating temperature to secure easy handling, such as pumping, of the dispersion. Additionally, the viscosity of the fat is important for obtaining a homogenous dispersion of bacteria in the fat. The viscosity of the fat of course also affects the sedimentation of bacteria in the dispersion.

A proper viscosity of the carrier is one way of reducing bacteria sedimentation in the dispersion. An additional way is by adding a dispersing agent, such as a surface-active agent or a steric stabiliser, and thereby obtaining a stable dispersion with minimal sedimentation.

Suitable surface-active agents are for example polysorbates (Tween®).

Polymers, such as polyacrylic acids, may be used as steric stabilisers.

The melting temperature of the fat should most preferably be at or below body temperature, i.e. 37° C., since the bacteria are easier released (and re-hydrated by body fluids) from the sanitary article at use when the fat is in its melted state.

However, the fat should mainly be in solid or semisolid state at ambient temperature (approximately 20-25° C.), since the sanitary article is easier to handle for e.g. the user if the fat does not flow or mess about. The loss of dispersion of bacteria during handling of the article is thus also decreased.

Due to these reasons the fat is preferably essentially solid below 25° C. and has a melting temperature between 25° C. and 45° C., more preferably 30-37° C. More particularly, the fat contains 15-70% solid phase at 20° C., and 0-30% at 30° C.

In view of adhesion it is better to use fat that is semi-solid at ambient temperature, rather than a solid fat.

It is preferred to use fat with an even melting curve. This may be achieved by using fat comprising a mixture of fats with different melting temperatures. For example a mixture of mono-, di- and triglycerides, which may be obtained either by esterfication of fatty acids of natural origin with glycerol or by transesterfication of natural fats.

Pure mono-, di- or triglycerides may also be used.

The fat may be of vegetable or animal origin.

A triglyceride with the following general formula may preferably be used:

$$\begin{array}{ccc} OH & OH & OH \\ | & | & | \\ C & -C & -C \\ | & | & | \\ A & A & A \end{array}$$

The substituent A may, for instance, be one of, or a combination of, $C_6$, $C_8$, $C_{10}$, $C_{12}$, $C_{14}$, $C_{16}$, $C_{18}$, $C_{20}$, $C_{22}$, and/or $C_{24}$ ($C_n$ means a carbon compound comprising n carbon atoms). A combination of different substituents result in several different melting temperatures, and if the substituents are properly chosen the result is an even melting curve.

Suitable fat is Akosoft® 36 from Karlshamns AB.

The bacteria are preferably applied as a step in the manufacturing of the sanitary article. It may be as a separate step or in combination with another step present in the manufacturing process. Furthermore, to reach optimal protection of the bacteria, the bacteria should preferably be applied in such a way that a major part of the bacteria are kept inside the final sanitary article.

The application may be on and/or in fibres, super-absorbents, a web, a sliver and/or a fabric.

The dispersion of bacteria is preferably applied to a web or a sliver in the manufacturing of a tampon. Most preferred is application onto a web.

The carrier is preferably essentially hydrophobic and should then comprise only a part of the final sanitary article, since the absorption otherwise would be disturbed. The body fluids, such as menstrual fluid or urine, which are to be absorbed by the sanitary article, are essentially hydrophilic, and if a large part of the article is made hydrophobic, the body fluid will be repelled and the absorption reduced. Therefore, to retain the absorbing properties of the sanitary article, the amount and the area and volume of applied carrier should be minimised. The dispersion is therefore preferably applied in at least one dot, spot, and/or continuous or discontinuous string (including a layer or a film).

However, it is preferred that the dispersion forms at least one continuous or discontinuous string in and/or on the final sanitary article.

Furthermore, a string is preferred in the viewpoint of bacteria survival. The bacteria in the string are surrounded by more carrier material than if the dispersion is spread over a larger area or volume by e.g. spraying, and the distance between one bacterium and another one is shorter. Thus, application of dispersion of bacteria in a string improves the shelf life of the sanitary article according to the present invention.

The string is preferably about 0.1-50 mm in diameter, more preferably 0.5-5 mm.

In addition, it might be advantageous to apply a wave shaped string. In a tampon, for instance, a controlled release effect might then be obtained. If wave shaped strings are applied on a sliver transverse to the direction of motion of the sliver (i e discontinuous application of several continuous strings), the dispersion will be distributed from the surface to the centre of the final tampon. Thus, the bacteria closest to the surface are released first, and the bacteria in the centre are released last.

The amount of fat is also important, apart from the aforementioned absorbing properties, for the manufacturing process. If too much fat is used, it may not be possible to form the sanitary article of interest in conventional machinery used for that purpose. The absorbing properties of an absorbing sanitary article are as previous mentioned also impaired by a large amount of fat.

Other additives known to the skilled person in the art may also be added to the dispersion.

For example, colouring agents and pigments may be added. For instance, metal oxides may be used and, for instance, zinc oxide and titanium oxide result in a dispersion with white colour. These substances mask the generally yellowish colour of the bacteria.

About 0.1-10% by weight of zinc oxide, titanium oxide or a mixture of these may be added to the dispersion.

The addition of zinc oxide, titanium oxide or a mixture of these affects the consistence of the dispersion making it more suitable for the process according to the present invention.

Nutrients to increase the survival and reproduction of bacteria and its production of lactic acid and other metabolites may also be added to the dispersion. Suitable nutrients are for example fermentable carbohydrates, such as lactulose, maltodextrine, dextrose, fructose, maltose, glucose, arabinose, mannose, galactose, salicin, etc. Vitamine B, vitamine E and complexes thereof are also suitable as nutrients.

About 1-30% by weight of nutrients may be added to the dispersion.

The lactic acid producing bacteria are preferably originating from the urogenital tract of a healthy woman with a normal flora of microorganisms.

Suitable lactic acid producing bacteria are, for instance, chosen from the group of bacteria strains consisting of *Pediococcus, Lactobacillus, Leuconostoc, Lactococcus, Aerococcus, Alloiococcus, Carnobacterium, Enterococcus, Streptococcus, Tetragenococcus,* and *Vagococcus.*

Furthermore, the bacteria are preferably selected amongst the group of bacteria strains consisting of *Pediococcus*, *Lactobacillus* and *Leuconostoc*.

Especially suitable bacteria are *P. acidilacti*, *P. pentosaceus*, *P. urinae*, *L. acidophilus*, *L. cristpatus*, *L. gasseri*, *L. vaginalis*, *L. mucosae*, *L. paracasei*, *L. plantarum*, *L. jensenii*, *L. casei*, *L. casei* subsp. *rhamnosus*, *L. fermentum*, and *L. johsonii*.

Preferably, a combination of some of these bacteria species is used according to the present invention. It is known in the art that a combination of different bacteria abbreviates the generation time of a bacterium, resulting in a rapid bacteria growth.

The bacteria are preferably freeze-dried before being dispersed in the carrier. Freeze-drying is a very gentle process compared to e.g. ordinary spray drying. Freeze-drying is for instance good at preserving protein structure. As is known to a skilled person in the art different additives may be mixed with the bacteria before freeze-drying. Such additives may be for example carbohydrates, but other additives are also possible.

After freeze-drying, and before dispersion in the carrier, it is feasible to sieve, or gentle grind, the freeze-dried bacteria to obtain a uniform particle size and reduce bacteria agglomeration. Agglomerates may otherwise get stuck in the extrusion nozzle. A more uniform dispersion is also obtained with a smaller bacteria particle size.

About 0.1-40% by weight of freeze-dried bacteria is preferably added to the carrier.

The process according to the present invention is particularly well suited for industrial practice. The dispersion of bacteria is easy to handle, e.g. to pump, and protects the bacteria as described above.

The present invention also relates to a process for the production of an absorbing sanitary article, e.g. a tampon, a sanitary napkin or a panty liner, comprising viable lactic acid producing bacteria, wherein the bacteria are dispersed in an essentially hydrophobic carrier and applied by any application method on and/or in at least one component that are to form part of the final article, and where the mentioned component(s) is/are fibres, super-absorbents, a web, a sliver and/or a fabric. The application may e.g. be spraying or gentle feeding (e.g. continuous or discontinuous extrusion).

Furthermore, the present invention relates to an absorbing sanitary article produced according to any one of the processes described above.

An absorbing sanitary article comprising at least one continuous or discontinuous string of bacteria dispersed in an essentially hydrophobic carrier is also comprised within the scope of the present invention.

The invention will now be illustrated by means of the following non-limiting examples.

Example 1

Preparation of the Dispersion

A freeze-dried bacteria pool comprising 17% by weight of *P. acidilactici* (approximately $950 \times 10^9$ cfu/g), 50% by weight of *L. casei* (approximately $300 \times 10^9$ cfu/g), 24% by weight of *L. johnsonii* (approximately $300 \times 10^9$ cfu/g), and 9% by weight of *L. fermentum* (approximately $200 \times 10^9$ cfu/g) was used. The total amount in the bacteria pool was approximately $460 \times 10^9$ cfu/g (cfu=colony forming units).

The freeze-dried bacteria were milled in a hammer mill and sieved through 0.75 mm. Analysis showed that about 98% of the bacteria had a particle size less than 0.35 mm.

Akosoft® 36 from Karlshamns AB was used as carrier. Akosoft® 36 is a vegetable fat from the coca-nut. The melting temperature is about 32-36° C. Furthermore, Akosoft® 36 has a very even melting curve.

The fat was first melted at about 50-70° C. and was thereafter slowly cooled to 30-38° C. to secure a homogenous mass.

5 g Tween® 80 (polysorbate 80) was mixed with 1 000 g Akosoft® 36.

95 g freeze-dried bacteria were thereafter added to the fat while stirring at a temperature of 30-38° C.

The dispersion was thereafter slowly cooled to approximately 20-30° C. The dispersion was stirred at regular intervals during cooling. If the cooling process is to rapid, large fat crystals are created, which result in a dispersion with a harder consistence.

The dispersion was then stored at 4-8° C.

Application:

The dispersion was tempered to about 20-30° C. before application. Thus, the dispersion had a temperature of about 20-30° C. during application.

The pumping of the dispersion was performed using a hydraulic piston pump. This type of pump is preferred since it does not affect the dispersion mechanically.

The dispersion was applied through a nozzle with a diameter of 0.78 mm, and extruded onto the web (along the direction of motion of the web) just before folding it to a sliver.

The tampon is thereafter manufactured by conventional manners.

The amount of dispersion added onto the web corresponds to about 150 mg ($6 \times 10^9$ cfu) in each tampon (about 20 cm of sliver).

Example 2

Absorption Test

The absorption of a tampon with a string of dispersion of bacteria, which was applied manually in the sliver before manufacturing of the tampon, was evaluated using the following test method.

Each tampon comprised about 150 mg Acosoft® 36.

The tampon was weighed, and dipped for 15 s in an artificial menstrual fluid at a temperature of 23° C. or 37° C. Thereafter, the tampon hang freely for 1 min, and was then weighed again. The amount of fluid absorbed by the tampon was calculated.

The results for the tampon with a string of dispersion of bacteria according to the present invention were compared to an ordinary tampon without dispersion of bacteria.

TABLE 1

| Sample | With fat | | Without fat |
|---|---|---|---|
| | 23° C. [g fluid/g tampon] | 37° C. [g fluid/g tampon] | 23° C. [g fluid/g tampon] |
| 1 | 8.12 | 10.8 | 7.01 |
| 2 | 5.23 | 10.08 | 7.46 |
| 3 | 5.40 | 9.96 | 7.61 |
| 4 | 7.07 | 12.28 | 7.19 |
| 5 | 7.88 | 10.25 | 7.08 |

It was noted that the absorption was delayed at 23° C. for the tampon with dispersion of bacteria. This was not the case at 37° C. since the fat melted at this temperature.

As can be seen from the table there is no difference in absorption when the dispersion of bacteria is added according to the invention.

Example 3

Application of a dispersion of bacteria was performed both manually and according to the present invention, i.e. as a step in an industrial tampon manufacturing process.

The carrier used in the dispersion was Akosoft® 36 from Karlshamns AB.

The dispersion contained about 9% by weight of bacteria. The bacteria mixture contained approximately $460 \times 10^9$ cfu/g bacteria. About 150 mg dispersion was applied in the tampon. This corresponds to 14 mg bacteria comprising approximately $6 \times 10^9$ cfu.

A) Manual application was performed using a syringe with a nozzle diameter of 1 mm. The sliver was opened and a continuous string of dispersion was applied manually inside the sliver. The sliver was then compressed between two rollers, and a tampon was made in the ordinary tampon manufacturing machinery.

B) Application by extrusion of the dispersion of bacteria according to the present invention was made onto a web during the tampon manufacturing.

The tampons were stored at room temperature (about 22° C.) for up to 8 months.

TABLE 2

| Storage at room temperature [months] | Manual application (A) [cfu] | Application by extrusion (B) [cfu] |
|---|---|---|
| 0 | $4.4 \times 10^8$ (100%) | $4.3 \times 10^8$ (100%) |
| 1 | $9.7 \times 10^7$ (22%) | — |
| 2 | — | $8.2 \times 10^7$ (19%) |
| 3.5 | — | $2.4 \times 10^7$ (5.6%) |
| 4.5 | $4.4 \times 10^7$ (10%) | — |
| 5.5 | $1.2 \times 10^7$ (2.7%) | — |
| 8 | — | $5.2 \times 10^6$ (1.2%) |

As can be seen in table 2, there is no significant difference with regard to stability of bacteria viability when the two application methods are compared. Thus, the process according to the present invention is not reducing bacteria activity, and therefore the resulting tampon has a long shelf life.

Extrapolation of these results gives that a minimum of about 0.5-1% (about $2-4 \times 10^6$) of the bacteria are still alive after a year of storage at room temperature. This amount is sufficient for providing the desired therapeutic effect, i e preservation and/or regeneration of a normal flora of microorganisms in the urogenital tract.

While the invention has been described in detail and with reference to specific embodiments thereof, it will be apparent for one skilled in the art that various changes and modifications can be made therein without departing from the spirit and scope thereof.

The invention claimed is:

1. A process for the production of an absorbing sanitary article comprising lactic acid producing bacteria comprising:
    dispersing viable lactic acid producing bacteria in an essentially hydrophobic carrier, resulting in a dispersion of bacteria; and
    extruding said dispersion of bacteria continuously or discontinuously onto, in or both onto and in at least one component that is to form part of the final article;
    wherein at least one extruded line of the dispersion of bacteria is on, in or both on and in the final sanitary article, said extruded line being continuous or discontinuous; and
    wherein the carrier has a viscosity of 200-20,000 mPas, measured at 30° C.

2. The process according to claim 1, wherein the absorbing sanitary article is a tampon.

3. The process according to claim 1, wherein the absorbing sanitary article is a sanitary napkin.

4. The process according to claim 1, wherein the absorbing sanitary article is a panty liner.

5. The process according to claim 1, wherein said at least one component is selected from the group consisting of cellulose fibers, viscose fibers, cellulose and viscose fibers, super-absorbents, a web, a sliver, and a fabric.

6. The process according to claim 1, wherein the line is wave shaped providing a controlled release of bacteria.

7. The process according to claim 1, wherein the carrier comprises fatty acids.

8. The process according to claim 7, wherein the carrier is at least partially saturated fat of mixtures or pure forms of mono-, di- and tri-glycerides, having a melting temperature between 25° C. and 45° C.

9. The process according to claim 1, wherein the dispersion of bacteria comprises a dispersion agent.

10. The process according to claim 1, wherein the dispersion of bacteria comprises a colouring agent or a pigment.

11. The process according to claim 10, wherein said colouring agent or pigment is a metal oxide.

12. The process according to claim 1, wherein the dispersion of bacteria comprises at least one nutrient for the bacteria.

13. The process according to claim 1, wherein the bacteria originate from urogenital tract of a woman with a normal flora of microorganisms.

14. The process according to claim 1, wherein the bacteria are selected from the group of bacteria strains consisting of *Pediococcus, Lactobacillus* and *Leuconostoc*.

15. The process according to claim 1, wherein the bacteria are freeze-dried.

16. An absorbing sanitary article comprising lactic acid producing bacteria wherein viable lactic acid producing bacteria are dispersed in an essentially hydrophobic carrier, and wherein the dispersion of bacteria forms at least one continuous or discontinuous extruded string on, in or both on and in the final sanitary article, wherein the continuous or discontinuous extruded string is a continuous or discontinuous extruded line, respectively, and only a part of the final sanitary article will comprise the dispersion of bacteria, and wherein the carrier has a viscosity of 200-20,000 mPas, measured at 30° C.

17. The absorbing sanitary article according to claim 16, wherein the absorbing sanitary article is a tampon.

18. The absorbing sanitary article according to claim 16, wherein the absorbing sanitary article is a sanitary napkin.

19. The absorbing sanitary article according to claim 16, wherein the absorbing sanitary article is a panty liner.

20. The absorbing sanitary article according to claim 16, wherein the essentially hydrophobic carrier comprises fatty acids.

21. The absorbing sanitary article according to claim 20, wherein the carrier is at least partially saturated fat of mixtures or pure forms of mono-, di- and tri-glycerides, having a melting temperature between 25° C. and 45° C.

22. The absorbing sanitary article according to claim 16, wherein the dispersion of bacteria comprises a colouring agent or a pigment.

23. The absorbing sanitary article according to claim 16, wherein the dispersion of bacteria comprises nutrients for the bacteria.

24. The absorbing sanitary article according to claim 16, wherein the bacteria originate from the urogential tract of a woman with a normal flora of microorganisms.

25. The absorbing sanitary article according to claim 16, wherein the bacteria are selected from the group of bacteria strains consisting of *Pediococcus, Lactobacillus* and *Leuconostoc*.

26. The absorbing sanitary article according to claim 16, wherein the bacteria are freeze-dried.

27. An absorbing sanitary article comprising lactic acid producing bacteria wherein essentially non-water containing viable lactic acid producing bacteria are dispersed in an essentially hydrophobic carrier, and wherein the essentially non-water containing dispersion of bacteria forms at least one continuous or discontinuous extruded string on, in or both on and in the final sanitary article, wherein the continuous or discontinuous extruded string is a continuous or discontinuous extruded line, respectively, and only a part of the final sanitary article will comprise the dispersion of bacteria, and wherein the carrier has a viscosity of 200-20,000 mPas, measured at 30° C.

28. The process according to claim 1, wherein the dispersion of bacteria is applied in such a way that a major part of the bacteria is kept inside the final absorbing sanitary article.

29. The process according to claim 1, wherein the carrier is a fat in semi-solid or solid form at ambient temperature.

30. The process according to claim 1, wherein only a part of the article comprises said dispersion of bacteria.

31. The process according to claim 1, wherein the bacteria originate from urogenital tract of a healthy woman with a normal flora of microorganisms.

32. The method according to claim 1, wherein said line is about 0.1 to 50 mm in diameter.

33. The method according to claim 1, wherein said line is about 0.5 to 5 mm in diameter.

34. The absorbing sanitary article according to claim 16, wherein a major part of the bacteria is inside the absorbing sanitary article.

35. The absorbing sanitary article according to claim 16, wherein the carrier is a fat in semi-solid or solid form at ambient temperature.

36. The absorbing sanitary article according to claim 16, wherein the bacteria originate from urogenital tract of a healthy woman with a normal flora of microorganisms.

37. The absorbing sanitary article according to claim 16, wherein said line is about 0.1 to 50 mm in diameter.

38. The absorbing sanitary article according to claim 16, wherein said line is about 0.5 to 5 mm in diameter.

39. The absorbing sanitary article according to claim 27, wherein a major part of the bacteria is inside the absorbing sanitary article.

40. The absorbing sanitary article according to claim 27, wherein the carrier is a fat in semi-solid or solid form at ambient temperature.

41. The absorbing sanitary article according to claim 27, wherein the bacteria originate from urogenital tract of a healthy woman with a normal flora of microorganisms.

42. The absorbing sanitary article according to claim 27, wherein said line is about 0.1 to 50 mm in diameter.

43. The absorbing sanitary article according to claim 27, wherein said line is about 0.5 to 5 mm in diameter.

44. The method according to claim 1, wherein said extruded line is continuously extruded.

45. The method according to claim 1, wherein said extruded line is discontinuously extruded.

46. The absorbing sanitary article according to claim 16, wherein the extruded line is continuous.

47. The absorbing sanitary article according to claim 16, wherein the extruded line is discontinuous.

48. The absorbing sanitary article according to claim 27, wherein the extruded line is continuous.

49. The absorbing sanitary article according to claim 27, wherein the extruded line is discontinuous.

50. The method according to claim 1, wherein the essentially hydrophobic carrier is essentially water-repellent.

51. The absorbing sanitary article according to claim 16, wherein the essentially hydrophobic carrier is essentially water-repellent.

52. The absorbing sanitary article according to claim 27, wherein the essentially hydrophobic carrier is essentially water-repellent.

53. The method according to claim 1, wherein said extruded dispersion of bacteria is not sprayed onto, in or both onto and in at least one component that is to form part of the final article.

54. The absorbing sanitary article according to claim 16, wherein the continuous or discontinuous extruded line is not a sprayed line.

55. The absorbing sanitary article according to claim 27, wherein the continuous or discontinuous extruded line is not a sprayed line.

56. The process according to claim 8, wherein the carrier has a melting point between approximately 30° C. and 45° C.

57. The process according to claim 56, wherein the carrier has a melting point between approximately 30° C. and 37° C.

58. The process according to claim 8, wherein the carrier has a viscosity of 200-3,000, measured at 30° C.

59. The process according to claim 7, wherein the carrier contains 15-70% solid phase at 20° C. and 0-30% at 30° C.

60. The process according to claim 8, wherein the carrier has a melting point between 30° C. and 37° C., a viscosity of 200-3,000, measured at 30° C., and contains 15-70% solid phase at 20° C. and 0-30% at 30° C.

61. The process according to claim 15, wherein 0.1-40 wt % of said bacteria is dispersed in said carrier.

62. The absorbing sanitary article according to claim 21, wherein the carrier has a melting point between approximately 30° C. and 45° C.

63. The absorbing sanitary article according to claim 62, wherein the carrier has a melting point between approximately 30° C. and 37° C.

64. The absorbing sanitary article according to claim 21, wherein the carrier has a viscosity of 200-3,000, measured at 30° C.

65. The absorbing sanitary article according to claim 20, wherein the carrier contains 15-70% solid phase at 20° C. and 0-30% at 30° C.

66. The absorbing sanitary article according to claim 21, wherein the carrier has a melting point between 30° C. and 37° C., a viscosity of 200-3,000, measured at 30° C., and contains 15-70% solid phase at 20° C. and 0-30% at 30° C.

67. The absorbing sanitary article according to claim 26, wherein 0.1-40 wt % of said bacteria is dispersed in said carrier.

* * * * *